Figure 1:
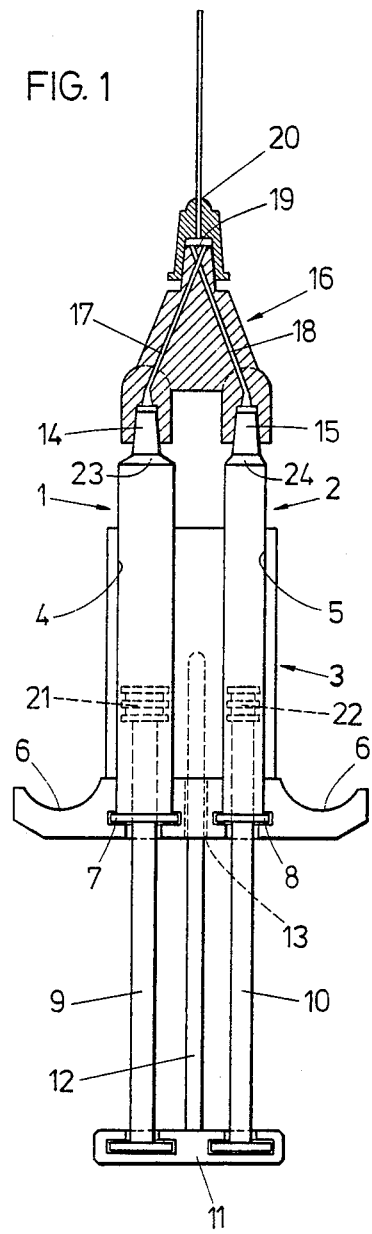

United States Patent [19]

Eibl et al.

[11] Patent Number: 4,735,616
[45] Date of Patent: Apr. 5, 1988

[54] ARRANGEMENT FOR APPLYING A TISSUE ADHESIVE

[75] Inventors: Johann Eibl; Thomas Seelich; Heinz Redl; Georg Habison, all of Vienna, Austria

[73] Assignee: Immuno Aktiengesellschaft fur Chemisch-Medizinische Produkte, Vienna, Austria

[21] Appl. No.: 875,080

[22] Filed: Jun. 17, 1986

[30] Foreign Application Priority Data

Jun. 20, 1985 [AT] Austria ................................ 1838/85

[51] Int. Cl.⁴ .............................................. A61M 5/08
[52] U.S. Cl. ...................................... 604/191; 604/90
[58] Field of Search ................ 604/191, 187, 218, 82, 604/89, 90

[56] References Cited

U.S. PATENT DOCUMENTS

| | | |
|---|---|---|
| 3,223,083 | 12/1965 | Cobey . |
| 4,040,420 | 8/1977 | Speer ...................... 604/191 |
| 4,359,049 | 11/1982 | Redl et al. . |
| 4,362,567 | 12/1982 | Schwarz et al. . |
| 4,414,976 | 11/1983 | Schwarz et al. . |

FOREIGN PATENT DOCUMENTS

| | | |
|---|---|---|
| 9324 | 10/1902 | Austria . |
| 379311 | 3/1984 | Austria . |
| 1182444 | 2/1985 | Canada . |
| 1051010 | 1/1954 | France . |

*Primary Examiner*—John D. Yasko
*Attorney, Agent, or Firm*—Burns, Doane, Swecker & Mathis

[57] ABSTRACT

An arrangement for applying a tissue adhesive based on human or animal proteins, to seamlessly or seam-supportingly connect human or animal tissue or organ parts by uniting with blood-clot-promoting coagulation factors (thrombin). The arrangement includes a plurality of syringe bodies commonly actuatable by pistons and to which a connecting head is attachable. The syringe bodies have equal effective strokes, yet one of them, i.e., that destined to contain the protein solution, has a cross sectional area that is two to nine times larger than the other one(s). There may be applied tissue adhesives having a fibrinogen content of from 2 to 12%.

10 Claims, 1 Drawing Sheet

U.S. Patent
Apr. 5, 1988
4,735,616

ARRANGEMENT FOR APPLYING A TISSUE ADHESIVE

The invention relates to an arrangement for applying a tissue adhesive based on human or animal proteins, to seamlessly or seam-supportingly connect human or animal tissue or organ parts, seal wounds, stop bleedings and the like, which tissue adhesive solidifies in situ by uniting with blood-clot-promoting coagulation factors. The arrangement comprises a plurality of syringe bodies ending in joining pieces and commonly actuatable by pistons to contain the components to be applied, wherein a connecting head is attachable to the joining pieces of the syringe bodies, which includes a separate conveying channel for each of the components to be applied and optionally for a medical propellant.

An arrangement of this type is described in U.S. Pat. No. 4,359,049. As components, a protein solution containing factor XIII and fibrinogen (tissue adhesive), on the one hand, and a solution containing thrombin, on the other hand, may be used. The components are mixed in a mixing needle attached to the connecting head and are applied onto the wound area to be treated or protected.

When realizing tissue adhesions or treatments, the protein solution and the thrombin solution usually are obtained by dissolving lyophilisates. In doing so, one may be faced with the problem, in particular in a surgical emergency situation, that the preparation of the protein solution takes an undesirably long time because of the poor solubility of these components. It is, of course, possible to shorten the dissolution time of the protein component by using a larger amount of solvent, yet, when mixing the protein solution with the thrombin solution at a volume ratio of 1:1, as has been common practice so far, even the clotting mixture is diluted to such an extent that a significant reduction in the ultimate tensile strength of the adhesion consequently will occur.

The invention aims at avoiding this difficulty and has as its object to design the known arrangement with a view to shortening the dissolution time when preparing a protein solution from a lyophilisate, without reducing the ultimate tensile strength of the adhesion.

In accordance with the invention, this object is achieved with an arrangement of the initially defined kind in that the syringe bodies have equal effective strokes, yet one of them, i.e., that destined to contain the protein solution, has a cross sectional area that is two to nine times larger than the other one(s). By effective stroke, the longitudinal extension of the syringe bodies containing the liquid components is meant, so that the volumes of the syringe bodies also are at a ratio of from 2:1 to 9:1.

According to a preferred embodiment, the syringe bodies may be designed as twin-chamber syringe bodies, with the protein and the thrombin components being stored in the mouth-side chambers in lyophilized form and the solvent being contained in the remaining chambers.

While the protein solutions used for tissue adhesions so far have had fibrinogen contents of about 10% (100 mg/ml) or more, diluted protein solutions with fibrinogen contents of from 2 to 7% may be used according to the invention, or there may be achieved adhesions of higher strengths when using protein solutions having fibrinogen contents of up to 12%.

The invention is based on the principle that a favorable ratio between the necessary reconstitution time of the protein lyophilisate and the strength of the adhesions will be obtained, if the hitherto usual mixing ratio of the protein solution and the thrombin solution of 1:1 is altered such that the protein component is dissolved in a relatively larger volume and the thrombin component is dissolved in a relatively smaller volume to compensate for the resulting lower protein concentration of the protein component in the mixture of the two components.

If, however, adhesions of particularly high strengths are sought, an increase in the concentration of the adhesive proteins may be obtained according to the invention after having mixed the two components, without having to put up with extended reconstitution times. Mixing the two components in a sufficiently exact ratio that deviates from 1 would be too difficult when using two separate syringes and has become possible only by the double syringe according to the invention.

Figure 2:
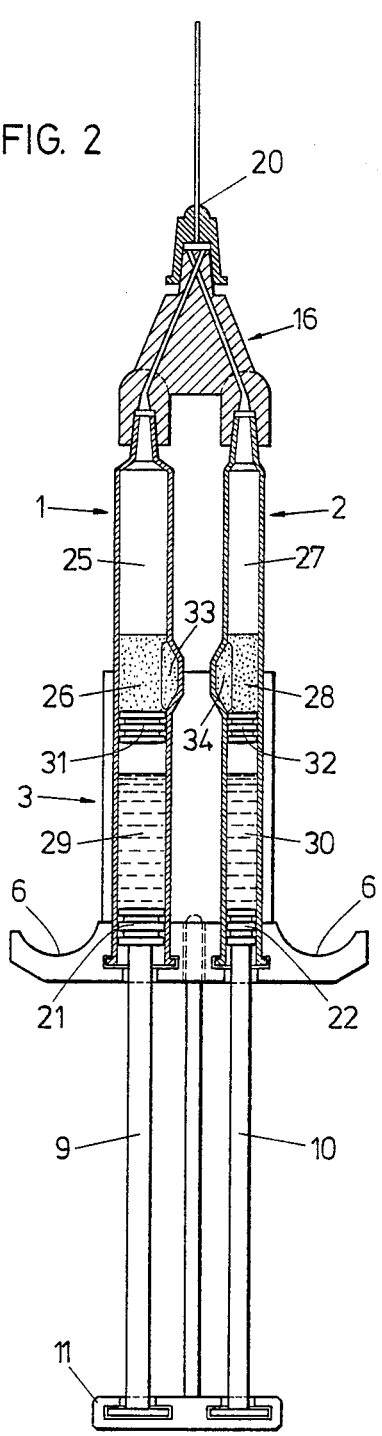

The arrangement according to the invention will now be explained in more detail by way of two embodiments and with reference to the accompanying drawing, wherein FIGS. 1 and 2 are each a partially sectioned side view of the double syringe according to the invention.

In FIG. 1, a syringe body 1 is destined to contain the protein solution and a syringe body 2 is destined to contain the thrombin solution. Suitably, they are designed as disposable syringe bodies, made of synthetic material. They are commonly inserted in U-shaped grooves 4, 5 of a holding means 3.

On the end of the holding means, finger grips 6 are provided, into which the flange ends 7 and 8 of the syringe bodies project such that the syringe bodies are fixed in the direction of their longitudinal axes. Pistons 21, 22 are guided in the syringe bodies, whose piston rods 9 and 10 project outwards. They comprise a common actuation means 11. A guiding rod 12 passes through a bore 13 of the holding means.

A connecting head 16 is attachable to the coni 14, 15 of the syringe bodies 1, 2 and includes conveying channels 17 and 18 ending in the front side 19 of the socket-like connecting head. A mixing needle 20 is attached to this socket.

As is apparent from the drawing, the syringe body 1 has a larger cross section than the syringe body 2; in the embodiment illustrated, the size ratio is 3:1, the volumes thus being 3:1. The effective strokes of the two syringe bodies, i.e., the respective distances of the piston 21 and 22 entered in broken lines from the mouth sides 23, 24, respectively, are identical.

With the modified embodiment according to FIG. 2, the syringe bodies are designed as twin-chamber syringe bodies, with the lyophilized adhesive protein 26 being filled in the mouth-side chamber 25 of the syringe body 1 and thrombin 28 being filled in the mouth-side chamber 27 of the syringe body 2. In chambers 29 and 30 facing away from the mouth sides, the solvent is contained, viz., a solution containing aprotinin in chamber 29 and a solution containing calcium chloride in chamber 30. Chambers 25 and 29 are separated by a floating piston 31, and chambers 27 and 30 are separated by a floating piston 32. By-passing ducts are denoted by 33 and 34.

The pistons 21 and 22 are fastened to piston rods 9 and 10. Upon actuation of the same, the liquid is urged from chambers 29, 30 into chambers 25 and 27, respectively, via the by-passing ducts, thus preparing the solutions required for application. Even with this embodiment, the cross sectional ratio of syringe body 1 to syringe body 2 is 3:1.

In the following Table, comparative assays are illustrated, wherein, according to column "Standard", an adhesive protein solution was mixed with a thrombin solution at a volume ratio of 1:1 in the conventional manner by using the arrangement known from U.S. Pat. No. 4,359,049; according to columns 2 to 9, adhesive protein solutions having different fibrinogen contents were mixed with thrombin solutions in different mixing ratios by using the mode of operation and arrangements according to the invention, and the properties of the solidified adhesives were investigated.

The assays were carried out with a lyophilized tissue adhesive according to U.S. Pat. No. 4,414,976, wherein the sterile lyophilized preparations (each containing 370 mg dry substance, 200 mg thereof fibrinogen) contained in final containers at first were dissolved by applying the method described in Canadian Pat. No. 1,182,444 with so much solvent (aqua ad iniectabilia or aprotinin solution) that the fibrinogen concentrations indicated in column 2 of the Table were obtained. The dissolution time required in each case was determined and is indicated in column 4 of the Table.

The tissue adhesive solutions (first component) obtained as described were rapidly mixed with a thrombin-CaCl$_2$ solution (second component) of the composition indicated in columns 5 and 6 at the volume ratio indicated in column 7 by using the application means according to the invention, were introduced into standardized separable casting molds and were incubated at 37° C. for 30 minutes. Subsequently, the solidified samples are removed from the casting molds, and the ultimate tensile strength was determined by means of an appropriate measuring device over a standardized cross section (0.0314 cm$^2$). The results obtained (mean values of three measurements each, the individual values deviating from the mean value by no more than 15%) are summarized in the last column of the Table.

In columns 8 to 11, the final concentrations of fibrinogen, aprotinin, thrombin and CaCl$_2$ upon mixture of the two components are indicated.

From the results, it becomes apparent that the dissolution time required depends on the desired fibrinogen concentration in the first component (tissue adhesive solution) prior to mixing the components, whereas the ultimate tensile strength depends on the final concentration of fibrinogen upon mixture of the two components.

Thus, it has become possible, by using the application means according to the invention, to shorten the dissolution time required without deteriorating the ultimate tensile strength (Examples 1, 2, 3, 5, 6, 7) or, vice versa, to further increase the ultimate tensile strength without having to put up with extended dissolution times (Examples 8 and 9). Example 4 indicates that in some cases in which a slightly reduced ultimate tensile strength will do, extremely short dissolution times may be reached by using the application means according to the invention.

Example 5 reveals that the application means according to the invention is suited also for application of high thrombin concentrations; however, solidification of the tissue adhesive in such a case occurs to rapidly that the casting of standardized clots and hence the determination of the ultimate tensile strength are no longer possible. Yet, the utilization of high thrombin concentrations is of great importance in surgical practice, in particular to stop bleedings.

A comparison of Examples 6 and 7 with Examples 1 to 3 finally proves that it is of no relevance either to the dissolution time required or to the ultimate tensile strength achieved, whether the dissolution of the lyophilized tissue adhesive is effected by means of aqua ad iniectabilia or by means of an aprotinin solution.

| Example No. | 1st Component: adhesive protein solution | | Reconstitution time min. | 2nd Component: Thrombin-CaCl$_2$ solution | | Mixing ratio 1st comp. 2nd comp. (v/v) | Final concentration upon mixing of the two components | | | | Ultimate tensile strength kPa+ |
|---|---|---|---|---|---|---|---|---|---|---|---|
| | Fibrinogen mg/ml | Aprotinin KIU/ml | | Thrombin IU/ml | CaCl$_2$ mmol/l | | Fibrinogen (mg/ml) | Aprotinin (KIU/ml) | Thrombin IU/ml | CaCl$_2$ mmol/l | |
| "Standard" | 100 | 3000 | 12 | 4 | 40 | 1:1 | 50 | 1500 | 2 | 20 | 155 |
| 1 | 67 | 2000 | 7 | 8 | 80 | 3:1 | 50 | 1500 | 2 | 20 | 163 |
| 2 | 60 | 1800 | 6 | 10 | 120 | 5:1 | 50 | 1500 | 1.7 | 20 | 155 |
| 3 | 56 | 1700 | 5–6(5,5) | 10 | 200 | 9:1 | 50 | 1530 | 1 | 20 | 152 |
| 4 | 30 | 1700 | 2–3(2,5) | 10 | 200 | 9:1 | 27 | 1530 | 1 | 20 | 89 |
| 5 | 56 | 1700 | 5–6(5,5) | 5000 | 200 | 9:1 | 50 | 1530 | 500 | 20 | not det. |
| 6 | 67 | — | 7 | 8 | 80 | 3:1 | 50 | — | 2 | 20 | 158 |
| 7 | 56 | — | 5 | 10 | 200 | 9:1 | 50 | — | 1 | 20 | 156 |
| 8 | 100 | 2000 | 12 | 8 | 80 | 3:1 | 75 | 1500 | 2 | 20 | 219 |
| 9 | 100 | 1700 | 12 | 10 | 200 | 9:1 | 90 | 1500 | 1 | 20 | 242 |

+1 kPa = 10.2 p · cm$^{-2}$

What we claim is:

1. An arrangement for applying a tissue adhesive that solidifies in situ by uniting with blood-clot-promoting coagulation factors, comprising:
   a plurality of syringe bodies ending in joining pieces;
   a piston in each of said plurality of syringe bodies for commonly actuating said syringe bodies;
   a connecting head attached to said joining pieces of said syringe bodies and provided with a separate conveying channel for each of the components to be applied;
   each of said syringe bodies having equal effective strokes; and
   one of said syringe bodies having a cross-sectional area that is two to nine times larger than the cross-sectional area of the remaining syringe bodies, said one syringe body containing an adhesive protein solution having a fibrinogen content of from 3 to 12%.

2. The arrangement of claim 1, wherein said adhesive protein solution is prepared from a lyophilisate.

3. The arrangement of claim 1, wherein a second of said plurality of syringe bodies contains a thrombin solution.

4. The arrangement of claim 1, further comprising:
first floating piston means in said one syringe body for dividing said one syringe body into a first chamber and a second chamber; and
first by-pass means in said one syringe body for allowing fluid from said second chamber to mix with fluid in said first chamber when said first floating piston means is adjacent said first by-pass means.

5. The arrangement of claim 4, further comprising:
second floating piston means in a second of said plurality of syringe bodies for dividing said second syringe body into a third chamber and a fourth chamber; and
second by-pass means in said second syringe body for allowing fluid from said fourth chamber to mix with fluid in said third chamber when said second floating piston means is adjacent said second by-pass means.

6. The device of claim 4, wherein said first chamber contains the adhesive protein solution and said second chamber contains a solvent including aprotinin.

7. The device of claim 5, wherein the third chamber contains thrombin and the fourth chamber contains a solvent including calcium chloride.

8. A device for dispensing a plurality of interreactable fluid, comprising:
a plurality of syringe bodies;
a connecting head interconnecting the discharge ends of each of the syringe bodies;
first piston means in each of said syringe bodies for actuating said syringe bodies;
first floating piston means in one of said syringe bodies for dividing said one syringe body into a first chamber and a second chamber; and
first by-pass means in said one syringe body for allowing fluid from said second chamber to mix with fluid in said first by-pass means in said one syringe body for allowing fluid from said second chamber to mix with fluid in said first chamber when said first floating piston means is adjacent said first by-pass means;
wherein said one syringe body has a cross-sectional area that is two to nine time larger than the cross-sectional area of the remaining syringe bodies.

9. The device of claim 8, further comprising:
second floating piston means in a second of said syringe bodies for dividing said second syringe body into third and fourth chambers;
second by-pass means in said second syringe body for allowing fluid from said fourth chamber to mix with fluid from said third chamber when said second floating piston means is adjacent said second by-pass means.

10. The device of claim 8, further comprising means for commonly actuating said first piston means.

* * * * *